US00PP11393P

United States Patent [19]

Kordes

[11] Patent Number: Plant 11,393

[45] Date of Patent: May 30, 2000

[54] HYBRID TEA ROSE PLANT NAMED 'KORSULAS'

[75] Inventor: Wilhelm Kordes, Sparrieshoop, Germany

[73] Assignee: Bear Creek Gardens, Inc., Medford, Oreg.

[21] Appl. No.: 09/161,118

[22] Filed: Sep. 25, 1998

[51] Int. Cl.[7] ..... A01H 5/00

[52] U.S. Cl. ..... Plt./134

[58] Field of Search ..... Plt./134, 145, 133

*Primary Examiner*—Howard J. Locker

*Attorney, Agent, or Firm*—Klarquist Sparkman Campbell Leigh & Whinston, LLP

[57] ABSTRACT

Hybrid tea rose plant having long stems; novel, greenish-yellow flower color in the bud; good vase life; moderate to strong fragrance; and good cut flower production.

1 Drawing Sheet

The present invention relates to a new and distinct variety of rose plant of the hybrid tea class which was originated by me by crossing two unnamed seedlings. The primary objective of this breeding was to produce a new rose variety having long stems, good cut flower production, a novel flower color, fragrance and good vase life. The objective was substantially achieved, along with other desirable improvements, as evidenced by the following unique combination of characteristics that are outstanding in the new variety and that distinguish it from its parents, as well as from all other varieties of which I am aware:

1. Long stems;
2. Novel greenish-yellow flower color in the bud;
3. Good vase life;
4. Fragrance; and
5. Good cut flower production.

'KORsulas' was bred and evaluated as a greenhouse cut flower rose. It produces on average 26" stems. Production per square meter of greenhouse is 160–170 per year. When combined with strong stems, novel color and fragrance it makes an exceptional cut flower rose. Asexual reproduction of this new variety by budding, as performed at Sparrieshoop, Germany and Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (Tamara×(Mabella×Goldy)).

*Pollen parent.*—Unnamed seedling (Champagne×Kabuki)×(Sunbeam×Evergold).

Classification:

*Botanical.*—Rosa hybrida.

*Commercial.*—Hybrid Tea.

FLOWER

Observations made from specimens grown in a greenhouse environment at Sparrieshoop, Germany and Somis, Calif., from January 1996 to September 1998.

Blooming Habit: Continuous.

Bud:

*Size.*—About 1¾ inches long when the petals start to unfurl.

*Form.*—The bud is long, pointed ovoid.

*Color.*—When sepals first divide, bud color is Yellow-Green Group 1D. When half blown, the upper sides of the petals are Yellow-Green Group 1D on the guard petals. The other petals are Yellow Group 13D on the outer ⅓ of each petal. The middle ⅓ of each petal is Yellow-Orange Group 14D while the inner ⅓ is Yellow Orange Group 14C. The lower sides of the petals are Yellow-Green Group 1D on the guard petals. The other petals are Yellow Group 13D on the outer ⅓ of each petal. The middle ⅓ of each petal is Yellow-Orange Group 14D while the inner ⅓ is Yellow-Orange Group 14C.

*Sepals.*—Color: Green Group 138C. Surface texture: Covered in fine hairs. There are three normally appendaged sepals. There are two unappendaged sepals with hairy edges.

*Receptacle.*—Color: Green Group 137D. Shape: Funnel. Size: Medium (7/16"×5/16"). Surface: Smooth.

*Peduncle.*—Length: Medium (2¾"). Surface: Smooth. Color: Green Group 137D. Strength: Stiff, erect.

Bloom:

*Size.*—Large. Average open size is 4½ inches.

*Borne.*—Singly.

*Stems.*—Strong. Average length is 26 inches.

*Form.*—When first open: High centered. Permanence: Retains its form to the end; outer petals curl back; some quilling.

*Petalage.*—Number of petals under normal conditions: 35.

*Color.*—The upper sides of the petals are Yellow Group 13D on the outer ⅓ of each petal. The middle ⅓ of each petal is Yellow-Orange Group 14D while the inner ⅓ of each petal is Yellow-Orange Group 14C. The reverse sides of the petals are Yellow Group 13D on the outer ⅓ of each petal while the middle ⅓ is Yellow-Orange Group 14D and the inner ⅓ is Yellow-Orange Group 14C. The base of each petal has a small (3/16"×3/16"), half moon of Yellow-Orange Group 14B at the point of attachment. The major color on the upper sides is Yellow-Orange Group 14C.

*Variegations.*—There are occasional green streaks along the midrib of the guard petals.

*Discoloration.*—At the end of the first day: Little change. At the end of the third day: Some change as the bud opens. The opening flower fades on the petal edges from Yellow-Orange Group 14C to Yellow Group 14D. This change stabilizes by day five of the flower and remains through the vase life of the flower 10–12 days.

*Fragrance.*—Moderate to strong anise with very sweet overtones.

Petals:

*Texture.*—Thick.

*Shape.*—Round to slightly deltoid.

*Form.*—Tips slightly recurved, edges slightly quilled on the outer petals.

*Arrangement.*—Imbricated. Petaloids in the center are few to none.

*Persistence.*—Petals drop off cleanly before drying.

*Lastingness.*—On the plant: Long (7–8 days). As a cut flower: Long (10–12 days).

Reproductive parts:

*Anthers.*—Size: Large. Quantity: Many. Color: Yellow-Orange Group 22A. Arrangement: Regular around styles.

*Filaments.*—Color: Yellow-Orange Group 14C.

*Pollen.*—Color: Gold-yellow.

*Styles.*—Color: Yellow Group 4C.

*Stigmas.*—Color: Yellow Group 4C.

Plant:

*Form.*—Bush.

*Growth.*—Vigorous; upright; branching. At maturity, after one year in a greenhouse environment, height is six feet, width is four feet.

Foliage: Number of leaflets on normal mid-stem leaves: Five.

*Size.*—Large (6 inches long×5¾ inches wide).

*Quantity.*—Abundant.

*Color.*—New foliage: Upper and lower surfaces: Greyed-Purple Group 183A. Old foliage: Upper surface: Green Group 139A. Lower surface: Green Group 139C.

*Shape.*—Broadly oval.

*Texture.*—Upper side: Smooth and matte.

*Edge.*—Serrated.

*Serration.*—Single, small.

*Petiole rachis.*—Color: Greyed-Purple Group 183C.

*Petiole underside.*—Smooth with an occasional prickle.

*Stipules.*—Long, (¾"), serrated, bearded.

*Disease resistance.*—Susceptible to mildew under normal growing conditions, in a greenhouse. Not tested for blackspot and rust.

Wood:

*New wood.*—Color: Green Group 137A. Bark: Smooth.

*Old wood.*—Color: Green Group 137B. Bark: Smooth.

Prickles:

*Quantity.*—On main canes from base: Ordinary. On laterals from main canes: Ordinary.

*Form.*—Medium, hooked downward.

*Color when young.*—Greyed-Orange Group 165C.

Small prickles:

*Quantity.*—On main stalks: None. On laterals: None.

I claim:

1. A new and distinct variety of hybrid tea rose plant as herein shown and described, characterized particularly by its long stems; novel, greenish-yellow flower color in the bud; good vase life; moderate to strong fragrance; and good cut flower production.

* * * * *

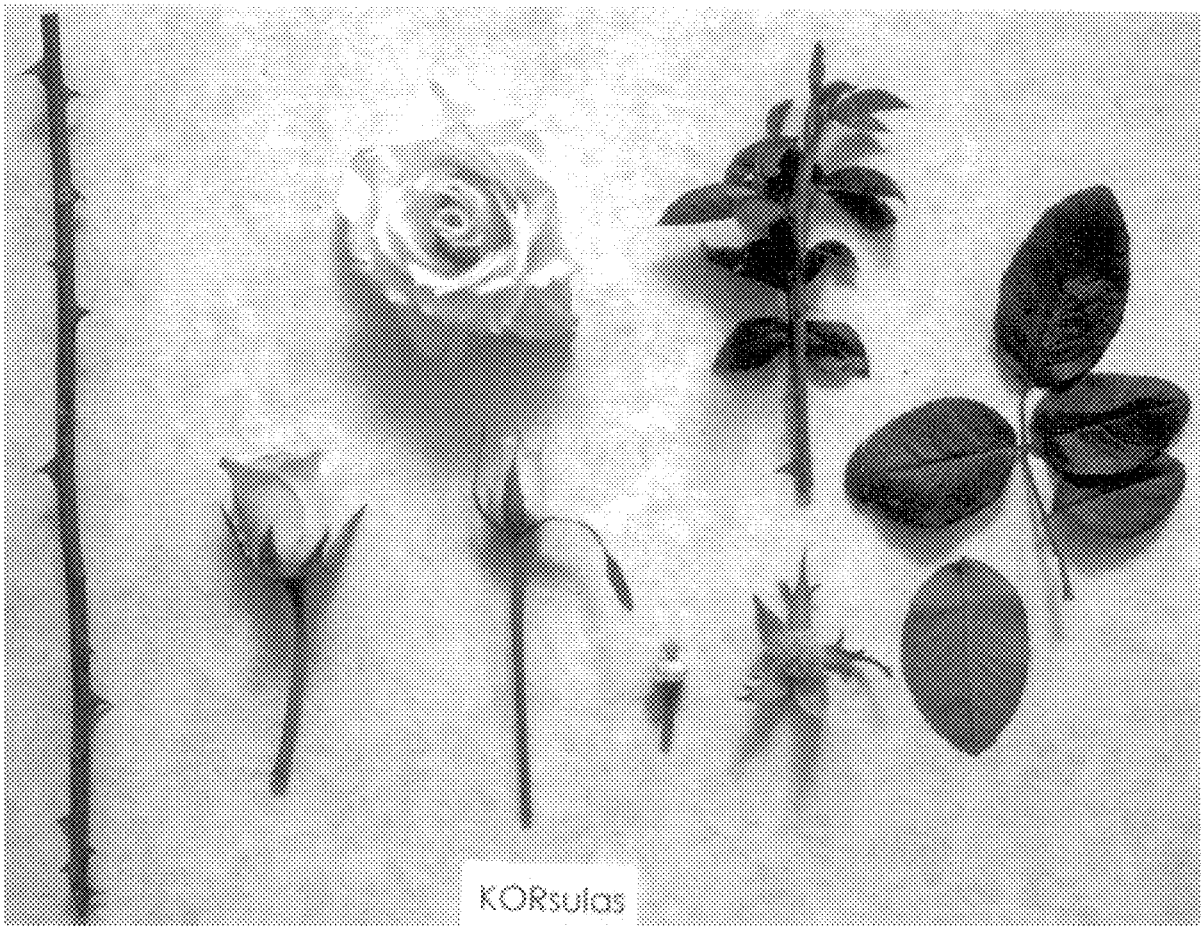
KORsulas